US005650557A

United States Patent [19]

Hannah et al.

[11] Patent Number: 5,650,557

[45] Date of Patent: *Jul. 22, 1997

[54] MATERIALS AND METHODS FOR INCREASING CORN SEED WEIGHT

[75] Inventors: L. Curtis Hannah, Gainesville, Fla.; Michael Giroux, Pullman, Wash.

[73] Assignee: University of Florida, Gainesville, Fla.

[*] Notice: The term of this patent shall not extend beyond the expiration date of Pat. No. 5,589,618.

[21] Appl. No.: 485,241

[22] Filed: Jun. 7, 1995

Related U.S. Application Data

[63] Continuation-in-part of Ser. No. 299,675, Sep. 1, 1994.

[51] Int. Cl.$^6$ .......................... C12N 15/05; C12N 15/11; A01H 5/00
[52] U.S. Cl. ...................... 800/205; 536/23.1; 536/23.2; 536/23.6; 435/172.3; 435/172.1; 935/9; 935/10
[58] Field of Search ...................... 800/208; 536/23.1, 536/23.2, 23.6; 935/9, 10; 435/172.3, 172.2

[56] References Cited

PUBLICATIONS

Bae, J.M., Giroux, L. Hannah (1990) "Cloning and Characterization of the Brittle–2 Gene of Maize" Maydica 35:317–322.

Anderson, J.M. et al. (1989) "The Encoded Primary Sequence of a Rice Seed ADP–glucose Pyrophosphorylase Subunit and its Homology to the Bacterial Enzyme" The Journal of Biology Chemistry 264(21):12238–12242.

Anderson, J.M. et al. (1991) "Molecular characterization of the gene encoding a rice endosperm–specific ADPglucose pyrophosphorylase subunit and its developmental pattern of transcription" Gene 97:199–205.

Copeland, Les, Jack Preiss (1981) "Purification of Spinach Leaf ADPglucose Pyrophosphorylase" Plant Physiol. 68:996–1001.

Dickinson, David B., Jack Preiss (1969) "Presence of ADP–glucose Pyrophosphorylase in Shrunken–2 and Brittle–2 Mutants of Maize Endosperm" Plant Physiol. 44:1058–1062.

Hannah, L. Curtis, Oliver E. Nelson, Jr. (1975) "Characterization of Adenosine Diphosphate Glucose Puyrophosphorylases from Developing Maize Seeds" Plant Physiol. 55:297–302.

Hannah, L.C., O.E. Nelson, Jr. (1976) "Characterization of ADP–Glucose Pyrophosphorylase from Shrunken–2 and Brittle–2 Mutants of Maize" Biochemical Genetics 14(7/80:547–560.

Lin, Tsan–Piao et al. (1988) "A Starch Deficient Mutant of Arabidopsis thaliana with Low ADPglucose Pyrophosphorylase Activity Lacks One of the Two Subunits of the Enzyme" Plant Physiol. 88:1175–1181.

Nakata, Paul A. et.al. (1991) "Comparison of the primary sequences of two potato tuber ADP–glucose pyrophosphorylase subunits" Plant Molecular Biology 17:1089–1093.

Okita, Thomas W. et al. (1990) "The Subunit Structure of Potato Tuber ADPglucose Pyrophosphorylase" Plant Physiol. 93:785–790.

Olive, Mark R. et al. (1989) "Isolation and nucleotide sequences of cDNA clones encosing ADP–glucose pyrophosphorylase polypeptides from wheat leaf and endosperm" Plant Molecular Biology 12:525–538.

Preiss, J. (1984) "Bacterial Glycogen Synthesis and Its Regulation" Ann. Rev. Microbiol. 38:419–458.

Tsai, Chia–Yin, Oliver E. Nelson (1966) "Starch–Deficient Maize Mutant Lacking Adenosine Diphosphate Glucose Pyrophosphorylases Activity" Science 151:341–343.

Shaw, Janine R., L. Curtis Hannah (1992) "Genomic Nucleotide Sequence of a Wild–Type Shrunken–2 Allele of Zea mays" Plant Physiol. 98:1214–1216.

Bhave, M.R. et al. (1990) "Identification and Molecular Characterization of Shrunken–2 cDNA Clones of Maize" The Plant Cell 2:581–588.

Muller–Rober, B.T. et al. (1990) "One of two different ADP–glucose pyrophosphorylase genes from potato responds strongly to elevated levels of sucrose" Mol. Gen. Genet. 224:136–146.

Morell, M., M. Bloom, J. Preiss (1988) "Affinity Labeling of the Allosteric Activator Site(s) of Spinach Leaf ADP–glucose Pyrophosphorylase" The Journal of Biological Chemistry 263(2):633–637.

Stark, D.M. et al. (1992) "Regulation of the Amount of Starch in Plant Tissues by ADP Glucose Pyrophosphorylase" Science 258:287–292.

Giroux, M.J. et al. (1994) "De novo synthesis of an intron by the maize transposable element Dissociation" Proc. Natl. Acad. Sci. USA 91:12150–12154.

*Primary Examiner*—Gary Benzion
*Attorney, Agent, or Firm*—Saliwanchik, Lloyd & Saliwanchik

[57] ABSTRACT

The subject invention pertains to novel variants of the maize gene, Shrunken2 (Sh2) and a method of using that gene. The variant gene, Sh2-m1Rev6, encodes a subunit of the ADP-glucose pyrophosphorylase (AGP) enzyme that has additional amino acids inserted in or near the allosteric binding site of the protein. Corn seed expressing the Sh2-m1Rev6 gene has a 15% weight increase over wild type seed. The increase in seed weight is not associated simply with an increase in percentage starch content of the seed.

12 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 7745 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TAAGAGGGGT  GCACCTAGCA  TAGATTTTTT  GGGCTCCCTG  GCCTCTCCTT  TCTTCCGCCT    60
GAAAACAACC  TACATGGATA  CATCTGCAAC  CAGAGGGAGT  ATCTGATGCT  TTTTCCTGGG   120
CAGGGAGAGC  TATGAGACGT  ATGTCCTCAA  AGCCACTTTG  CATTGTGTGA  AACCAATATC   180
GATCTTTGTT  ACTTCATCAT  GCATGAACAT  TTGTGGAAAC  TACTAGCTTA  CAAGCATTAG   240
TGACAGCTCA  GAAAAAAGTT  ATCTCTGAAA  GGTTTCATGT  GTACCGTGGG  AAATGAGAAA   300
TGTTGCCAAC  TCAAACACCT  TCAATATGTT  GTTTGCAGGC  AAACTCTTCT  GGAAGAAAGG   360
TGTCTAAAAC  TATGAACGGG  TTACAGAAAG  GTATAAACCA  CGGCTGTGCA  TTTTGGAAGT   420
ATCATCTATA  GATGTCTGTT  GAGGGGAAAG  CCGTACGCCA  ACGTTATTTA  CTCAGAAACA   480
GCTTCAACAC  ACAGTTGTCT  GCTTTATGAT  GGCATCTCCA  CCCAGGCACC  CACCATCACC   540
TATTCACCTA  TCTCTCGTGC  CTGTTTATTT  TCTTGCCCTT  TCTGATCATA  AAAAATCATT   600
AAGAGTTTGC  AAACATGCAT  AGGCATATCA  ATATGCTCAT  TTATTAATTT  GCTAGCAGAT   660
CATCTTCCTA  CTCTTTACTT  TATTTATTGT  TTGAAAAATA  TGTCCTGCAC  CTAGGGAGCT   720
CGTATACAGT  ACCAATGCAT  CTTCATTAAA  TGTGAATTTC  AGAAAGGAAG  TAGGAACCTA   780
TGAGAGTATT  TTTCAAAATT  AATTAGCGGC  TTCTATTATG  TTTATAGCAA  AGGCCAAGGG   840
CAAAATCGGA  ACACTAATGA  TGGTTGGTTG  CATGAGTCTG  TCGATTACTT  GCAAGAAATG   900
TGAACCTTTG  TTTCTGTGCG  TGGGCATAAA  ACAAACAGCT  TCTAGCCTCT  TTTACGGTAC   960
TTGCACTTGC  AAGAAATGTG  AACTCCTTTT  CATTTCTGTA  TGTGGACATA  ATGCCAAAGC  1020
ATCCAGGCTT  TTTCATGGTT  GTTGATGTCT  TTACACAGTT  CATCTCCACC  AGTATGCCCT  1080
CCTCATACTC  TATATAAACA  CATCAACAGC  ATCGCAATTA  GCCACAAGAT  CACTTCGGGA  1140
GGCAAGTGTG  ATTTCGACCT  TGCAGCCACC  TTTTTTTGTT  CTGTTGTAAG  TATACTTTCC  1200
CTTACCATCT  TTATCTGTTA  GTTTAATTTG  TAATTGGGAA  GTATTAGTGG  AAAGAGGATG  1260
AGATGCTATC  ATCTATGTAC  TCTGCAAATG  CATCTGACGT  TATATGGGCT  GCTTCATATA  1320
ATTTGAATTG  CTCCATTCTT  GCCGACAATA  TATTGCAAGG  TATATGCCTA  GTTCCATCAA  1380
AAGTTCTGTT  TTTTCATTCT  AAAAGCATTT  TAGTGGCACG  CAATTTTGTC  CATGAGGGAA  1440
AGGAAATCTG  TTTTGGTTAC  TTTGCTTGAG  GTGCATTCTT  CATATGTCCA  GTTTTATGGA  1500
```

-continued

```
AGTAATAAAC TTCAGTTTGG TCATAAGATG TCATATTAAA GGGCAAACAT ATATTCAATG    1560
TTCAATTCAT CGTAAATGTT CCCTTTTTGT AAAAGATTGC ATACTCATTT ATTGAGTTG     1620
CAGGTGTATC TAGTAGTTGG AGGAGATATG CAGTTGCAC TTGCATTGGA CACGAACTCA     1680
GGTCCTCACC AGATAAGATC TTGTGAGGGT GATGGGATTG ACAGGTTGGA AAAATTAAGT   1740
ATTGGGGGCA GAAAGCAGGA GAAAGCTTTG AGAAATAGGT GCTTGGTGG TAGAGTTGCT    1800
GCAACTACAC AATGTATTCT TACCTCAGAT GCTTGTCCTG AAACTCTTGT AAGTATCCAC   1860
CTCAATTATT ACTCTTACAT GTTGGTTTAC TTTACGTTTG TCTTTTCAAG GGAAATTTAC   1920
TGTATTTTTT GTGTTTTGTG GGAGTTCTAT ACTTCTGTTG GACTGGTTAT TGTAAAGATT   1980
TGTTCAAATA GGGTCATCTA ATAATTGTTT GAAATCTGGG AACTGTGGTT TCACTGCGTT   2040
CAGGAAAAAG TGAATTATTG GTTACTGCAT GAATAACTTA TGGAAATAGA CCTTAGAGTT   2100
GCTGCATGAT TATCACAAAT CATTGCTACG ATATCTTATA ATAGTTCTTT CGACCTCGCA   2160
TTACATATAT AACTGCAACT CCTAGTTGCG TTCAAAAAAA AAAATGCAAC TCTTAGAACG   2220
CTCACCAGTG TAATCTTTCC TGAATTGTTA TTAATGGCA TGTATGCACT ACTTGTATAC    2280
TTATCTAGGA TTAAGTAATC TAACTCTAGG CCCCATATTT GCAGCATTCT CAAACACAGT   2340
CCTCTAGGAA AAATTATGCT GATGCAAACC GTGTATCTGC TATCATTTG GGCGGAGGCA    2400
CTGGATCTCA GCTCTTTCCT CTGACAAGCA CAAGAGCTAC GCCTGCTGTA AGGGATAACA   2460
CTGAACATCC AACGTTGATT ACTCTATTAT AGTATTATAC AGACTGTACT TTTCGAATTT   2520
ATCTTAGTTT CTACAATAT TTAGTGGATT CTTCTCATTT TCAAGATACA CAATTGATCC    2580
ATAATCGAAG TGGTATGTAA GACAGTGAGT TAAAAGATTA TATTTTTGG GAGACTTCCA    2640
GTCAAATTTT CTTAGAAGTT TTTTGGTCC AGATGTTCAT AAAGTCGCCG CTTTCATACT    2700
TTTTTAATT TTTAATTGG TGCACTATTA GGTACCTGTT GGAGGATGTT ACAGGCTTAT     2760
TGATATCCCT ATGAGTAACT GCTTCAACAG TGGTATAAAT AAGATATTTG TGATGAGTCA   2820
GTTCAATTCT ACTTCGCTTA ACCGCCATAT TCATCGTACA TACCTTGAAG GCGGGATCAA   2880
CTTTGCTGAT GGATCTGTAC AGGTGATTTA CCTCATCTTG TTGATGTGTA ATACTGTAAT   2940
TAGGAGTAGA TTTGTGTGGA GAGAATAATA AACAGATGCC GAGATTCTTT TCTAAAAGTC   3000
TAGATCCAAA GGCATTGTGG TTCAAAACAC TATGGACTTC TACCATTTAT GTCATTACTT   3060
TGCCTTAATG TTCCATTGAA TGGGGCAAAT TATTGATTCT ACAAGTGTTT AATTAAAAAC   3120
TAATTGTTCA TCCTGCAGGT ATTAGCGGCT ACACAAATGC CTGAAGAGCC AGCTGGATGG   3180
TTCCAGGGTA CAGCAGACTC TATCAGAAAA TTTATCTGGG TACTCGAGGT AGTTGATATT   3240
TTCTCGTTTA TGAATGTCCA TTCACTCATT CCTGTAGCAT GTTTCTTTG TAATTTTGAG    3300
TTCTCCTGTA TTTCTTTAGG ATTATTACAG TCACAAATCC ATTGACAACA TTGTAATCTT   3360
GAGTGGCGAT CAGCTTATC GGATGAATTA CATGGAACTT GTGCAGGTAT GGTGTTCTCT    3420
TGTTCCTCAT GTTTCACGTA ATGTCCTGAT TTGGATTAA CCAACTACTT TTGGCATGCA    3480
TTATTCCAG AAACATGTCG AGGACGATGC TGATATCACT ATATCATGTG CTCCTGTTGA    3540
TGAGAGGTAA TCAGTTGTTT ATATCATCCT AATATGAATA TGTCATCTTG TTATCCAACA   3600
CAGGATGCAT ATGGTCTAAT CTGCTTTCCT TTTTTTTCCC TTCGGAAGCC GAGCTTCTAA   3660
AAATGGGCTA GTGAAGATTG ATCATACTGG ACGTGTACTT CAATTCTTTG AAAAACCAAA   3720
GGGTGCTGAT TTGAATTCTA TGGTTAGAAA TTCCTTGTGT AATCCAATTC TTTTGTTTTC   3780
CTTTCTTTCT TGAGATGAAC CCCTCTTTTA GTTATTTCCA TGGATAACCT GTACTTGACT   3840
TATTCAGAAA TGATTTTCTA TTTTGCTGTA GAATCTGACA CTAAAGCTAA TAGCACTGAT   3900
```

```
GTTGCAGAGA GTTGAGACCA ACTTCCTGAG CTATGCTATA GATGATGCAC AGAAATATCC  3960
ATACCTTGCA TCAATGGGCA TTTATGTCTT CAAGAAAGAT GCACTTTTAG ACCTTCTCAA  4020
GTAATCACTT TCCTGTGACT TATTTCTATC CAACTCCTAG TTTACCTTCT AACAGTGTCA  4080
ATTCTTAGGT CAAAATATAC TCAATTACAT GACTTTGGAT CTGAAATCCT CCCAAGAGCT  4140
GTACTAGATC ATAGTGTGCA GGTAAGTCTG ATCTGTCTGG AGTATGTGTT CTGTAAACTG  4200
TAAATTCTTC ATGTCAAAAA GTTGTTTTTG TTTCCAGTTT CCACTACCAA TGCACGATTT  4260
ATGTATTTTC GCTTCCATGC ATCATACATA CTAACAATAC ATTTACGTA TTGTGTTAGG  4320
CATGCATTTT TACGGGCTAT TGGGAGGATG TTGGAACAAT CAAATCATTC TTTGATGCAA  4380
ACTTGGCCCT CACTGAGCAG GTACTCTGTC ATGTATTCTG TACTGCATAT ATATTACCTG  4440
GAATTCAATG CATAGAATGT GTTAGACCAT CTTAGTTCCA TCCTGTTTTC TTCAATTAGC  4500
TTATCATTTA ATAGTTGTTG GCTAGAATTT AAACACAAAT TACCTAATA TGTTTCTCTC   4560
TTCAGCCTTC CAAGTTTGAT TTTTACGATC CAAAAACACC TTTCTTCACT GCACCCCGAT  4620
GCTTGCCTCC GACGCAATTG GACAAGTGCA AGGTATATGT CTTACTGAGC ACAATTGTTA  4680
CCTGAGCAAG ATTTTGTGTA CTTGACTTGT TCTCCTCCAC AGATGAAATA TGCATTTATC  4740
TCAGATGGTT GCTTACTGAG AGAATGCAAC ATCGAGCATT CTGTGATTGG AGTCTGCTCA  4800
CGTGTCAGCT CTGGATGTGA ACTCAAGGTA CATACTCTGC CAATGTATCT ACTCTTGAGT  4860
ATACCATTTC AACACCAAGC ATCACCAAAT CACACAGAAC AATAGCAACA AAGCCTTTTA  4920
GTTCCAAGCA ATTTAGGGTA GCCTAGAGTT GAAATCTAAC AAAACAAAAG TCAAAGCTCT  4980
ATCACGTGGA TAGTTGTTTT CCATGCACTC TTATTTAAGC TAATTTTTTG GGTATACTAC  5040
ATCCATTTAA TTATTGTTTT ATTGCTTCTT CCCTTTGCCT TTCCCCATT ACTATCGCGT   5100
CTTAAGATCA TACTACGCAC TAGTGTCTTT AGAGGTCTCT GGTGGACATG TTCAAACCAT  5160
CTCAATCGGT GTTGGACAAG TTTTTCTTGA ATTGTGCTA CACCTAACCT ATCACGTATG   5220
TCATCGTTTC AAACTCGATC CTTCCTGTAT CATCATAAAT CCAATGCAAC ATACGCATTT  5280
ATGCAACATT TATCTGTTGA ACATGTCATC TTTTGTAGG TTAACATTAT GCACCATACA   5340
ATGTAGCATG TCTAATCATC ATCCTATAAA ATTTACATTT TAGCTTATGT GGTATCCTCT  5400
TGCCACTTAG AACACCATAT GCTTGATGCC ATTTCATCCA CCCTGCTTTG ATTCTATGGC  5460
TAACATCTTC ATTAATATCC TCGCCTCTCT GTATCATTGG TCCTAAATAT GGAAATACAT  5520
TCTTTCTGGG CACTACTTGA CCTTCCAAAC TAACGTCTCC TTTGCTCCTT TCTTGTGTGT  5580
AGTAGTACCG AAGTCACATC TCATATATTC GGTTTTAGTT CTACTAAGTC CCGGGTTCGA  5640
TCCCCCTCAG GGGTGAATTT CGGGCTTGGT AAAAAAAATC CCCTCGCTGT GTCCCGCCCG  5700
CTCTCGGGGA TCGATATCCT GCGCGCCACC CTCCGGCTGG GCATTGCAGA GTGAGCAGTT  5760
GATCGGCTCG TTAGTGATGG GGAGCGGGGT TCAAGGGTTT TCTCGGCCGG GACCATGTTT  5820
CGGTCTCTTA ATATAATGCC GGGAGGGCAG TCTTTCCCTC CCCGGTCGAG TTTTAGTTCT  5880
ACCGAGTCTA AAACCTTTGG ACTCTAGAGT CCCCTGTCAC AACTCACAAC TCTAGTTTTC  5940
TATTTACTTC TACCTAGCGT TTATTAATGA TCACTATATC GTCTGTAAAA AGCATACACC  6000
AATGTAATCC CCTTGTATGT CCCTTGTAAT ATTATCCATC ACAAGAAAAA AAGGTAAGGC  6060
TCAAAGTTGA CTTTTGATAT AGTCCTATTC TAATCGAGAA GTCATCTGTA TCTTCGTCTC  6120
TTGTTCGAAC ACTAGTCACA AAATTTTTTG TACATGTTCT TAATGAGTCC AACGTAATAT  6180
TCCTTGATAT TTTGTCATAA GCCCTCATCA AGTCAATGAA AATCACGTGT AGGTCCTTCA  6240
TTTGTTCCTT ATACTGCTCC ATCACTTGTC TCATTAAGAA AATCTCTCTC ATAGTTAACC  6300
```

| | | | | | |
|---|---|---|---|---|---|
|TTTTGGCATG|AAACAAAATC|ACACAGAAGT|TGTTTCCTTT|TTTTAAGATC|CCACACAAAA 6360|
|GAGGTTTGAT|CTAAGGAATC|TGGATCCCTG|ACAGGTTTAT|CAAAATCCTT|TGTGTTTTTC 6420|
|TTAAAACTGA|ATATTCCTCC|AGCTTCTAGT|ATTGATGTAA|TATTCAATCT|GTTTAGCAAG 6480|
|TGAACACCTT|GGTTCTTGTT|GTTACTGTAC|CCCCCCCCCC|CCCCCCCCCC|CGAGGCCCAG 6540|
|ATTACCACGA|CATGAATACA|AGAATATTGA|ACCCAGATCT|AGAGTTTGTT|TGTACTGTTG 6600|
|AAAATCGGTG|ACAATTCATT|TTGTTATTGC|GCTTTCTGAT|AACGACAGGA|CTCCGTGATG 6660|
|ATGGGAGCGG|ACACCTATGA|AACTGAAGAA|GAAGCTTCAA|AGCTACTGTT|AGCTGGGAAG 6720|
|GTCCCAGTTG|GAATAGGAAG|GAACACAAAG|ATAAGGTGAG|TATGGATGTG|GAACCACCGG 6780|
|TTAGTTCCCA|AAAATATCAC|TCACTGATAC|CTGATGGTAT|CCTCTGATTA|TTTTCAGGAA 6840|
|CTGTATCATT|GACATGAATG|CTAGGATTGG|GAAGAACGTG|GTGATCACAA|ACAGTAAGGT 6900|
|GAGCGAGCGC|ACCTACATGG|GTGCAGAATC|TTGTGTGCTC|ATCTATCCTA|ATTCGGTAAT 6960|
|TCCTATCCAG|CGCTAGTCTT|GTGACCATGG|GGCATGGGTT|CGACTCTGTG|ACAGGGCATC 7020|
|CAAGAGGCTG|ATCACCCGGA|AGAAGGGTAC|TCGTACTACA|TAAGGTCTGG|AATCGTGGTG 7080|
|ATCTTGAAGA|ATGCAACCAT|CAACGATGGG|TCTGTCATAT|AGATCGGCTG|CGTGTGCGTC 7140|
|TACAAAACAA|GAACCTACAA|TGGTATTGCA|TCGATGGATC|GTGTAACCTT|GGTATGGTAA 7200|
|GAGCCGCTTG|ACAGAAAGTC|GAGCGTTCGG|GCAAGATGCG|TAGTCTGGCA|TGCTGTTCCT 7260|
|TGACCATTTG|TGCTGCTAGT|ATGTACTGTT|ATAAGCTGCC|CTAGAAGTTG|CAGCAAACCT 7320|
|TTTTATGAAC|CTTTGTATTT|CCATTACCTG|CTTGGATCA|ACTATATCTG|TCATCCTATA 7380|
|TATTACTAAA|TTTTTACGTG|TTTTTCTAAT|TCGGTGCTGC|TTTTGGGATC|TGGCTTCGAT 7440|
|GACCGCTCGA|CCCTGGGCCA|TTGGTTCAGC|TCTGTTCCTT|AGAGCAACTC|CAAGGAGTCC 7500|
|TAAATTTGT|ATTAGATACG|AAGGACTTCA|GCCGTGTATG|TCGTCCTCAC|CAAACGCTCT 7560|
|TTTTGCATAG|TGCAGGGGTT|GTAGACTTGT|AGCCCTTGTT|TAAAGAGGAA|TTTGAATATC 7620|
|AAATTATAAG|TATTAAATAT|ATATTAATT|AGGTTAACAA|ATTTGGCTCG|TTTTTAGTCT 7680|
|TTATTTATGT|AATTAGTTTT|AAAAATAGAC|CTATATTTCA|ATACGAAATA|TCATTAACAT 7740|
|CGATA| | | | | 7745|

( 2 ) INFORMATION FOR SEQ ID NO:2:

( i ) SEQUENCE CHARACTERISTICS:
        ( A ) LENGTH: 1919 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
|ACAAGATCAC|TTCGGGAGGC|AAGTGCGATT|TTGATCTTGC|AGCCACCTTT|TTTTGTTCTG 60|
|TTGTGTATCT|AGTAGTTGGA|GGAGATATGC|AGTTTGCACT|TGCATTGGAC|ACGAACTCAG 120|
|GTCCTCACCA|GATAAGATCT|TGTGAGGGTG|ATGGGATTGA|CAGGTTGGAA|AAATTAAGTA 180|
|TTGGGGGCAG|AAAGCAGGAG|AAAGCTTTGA|GAAATAGGTG|CTTTGGTGGT|AGAGTTGCTG 240|
|CAACTACACA|ATGTATTCTT|ACCTCAGATG|CTTGTCCTGA|AACTCTTCAT|TCTCAAACAC 300|
|AGTCCTCTAG|GAAAAATTAT|GCTGATGCAA|ACCGTGTATC|TGCGATCATT|TTGGGCGGAG 360|
|GCACTGGATC|TCAGCTCTTT|CCTCTGACAA|GCACAAGAGC|TACGCCTGCT|GTACCTGTTG 420|
|GAGGATGTTA|CAGGCTTATT|GATATCCCTA|TGAGTAACTG|CTTCAACAGT|GGTATAAATA 480|

-continued

```
AGATATTTGT GATGAGTCAG TTCAATTCTA CTTCGCTTAA CCGCCATATT CATCGTACAT      540
ACCTTGAAGG CGGGATCAAC TTTGCTGATG GATCTGTACA GGTATTAGCG GCTACACAAA      600
TGCCTGAAGA GCCAGCTGGA TGGTTCCAGG GTACAGCAGA CTCTATCAGA AAATTTATCT      660
GGGTACTCGA GGATTATTAC AGTCACAAAT CCATTGACAA CATTGTAATC TTGAGTGGCG      720
ATCAGCTTTA TCGGATGAAT TACATGGAAC TTGTGCAGAA ACATGTCGAG GACGATGCTG      780
ATATCACTAT ATCATGTGCT CCTGTTGATG AGAGCCGAGC TTCTAAAAAT GGGCTAGTGA      840
AGATTGATCA TACTGGACGT GTACTTCAAT TCTTTGAAAA ACCAAAGGGT GCTGATTTGA      900
ATTCTATGAG AGTTGAGACC AACTTCCTGA GCTATGCTAT AGATGATGCA CAGAAATATC      960
CATACCTTGC ATCAATGGGC ATTTATGTCT TCAAGAAAGA TGCACTTTTA GACCTTCTCA     1020
AGTCAAAATA TACTCAATTA CATGACTTTG GATCTGAAAT CCTCCCAAGA GCTGTACTAG     1080
ATCATAGTGT GCAGGCATGC ATTTTACGG GCTATTGGGA GGATGTTGGA ACAATCAAAT      1140
CATTCTTTGA TGCAAACTTG GCCCTCACTG AGCAGCCTTC CAAGTTTGAT TTTTACGATC     1200
CAAAAACACC TTTCTTCACT GCACCCCGAT GCTTGCCTCC GACGCAATTG GACAAGTGCA     1260
AGATGAAATA TGCATTTATC TCAGATGGTT GCTTACTGAG GAATGCAAC ATCGAGCATT      1320
CTGTGATTGG AGTCTGCTCA CGTGTCAGCT CTGGATGTGA ACTCAAGGAC TCCGTGATGA     1380
TGGGAGCGGA CATCTATGAA ACTGAAGAAG AAGCTTCAAA GCTACTGTTA GCTGGGAAGG     1440
TCCCGATTGG AATAGGAAGG AACACAAAGA TAAGGAACTG TATCATTGAC ATGAATGCTA     1500
GGATTGGGAA GAACGTGGTG ATCACAAACA GTAAGGGCAT CCAAGAGGCT GATCACCCGG     1560
AAGAAGGGTA CTCGTACTAC ATAAGGTCTG GAATCGTGGT GATCCTGAAG AATGCAACCA     1620
TCAACGATGG GTCTGTCATA TAGATCGGCT GCGTTTGCGT CTACAAAACA AGAACCTACA     1680
ATGGTATTGC ATCGATGGAT CGTGTAACCT TGGTATGGTA AGAGCCGCTT GACAGGAAGT     1740
CGAGCTTCGG GCGAAGATGC TAGTCTGGCA TGCTGTTCCT TGACCATTTG TGCTGCTAGT     1800
ATGTACCTGT TATAAGCTGC CCTAGAAGTT GCAGCAAACC TTTTTATGAA CCTTTGTATT     1860
TCCATTACCC TGCTTTGGAT CAACTATATC TGTCAGTCCT ATATATTACT AAATTTTTA     1919
```

( 2 ) INFORMATION FOR SEQ ID NO:3:

( i ) SEQUENCE CHARACTERISTICS:
        ( A ) LENGTH: 518 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met Gln Phe Ala Leu Ala Leu Asp Thr Asn Ser Gly Pro His Gln Ile
 1               5                  10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Gly Thr Gly Ser Gln
                85                  90                  95

Leu Phe Pro Leu Thr Ser Thr Arg Ala Thr Pro Ala Val Pro Val Gly
```

```
                          100                      105                      110
        Gly Cys Tyr Arg Leu Ile Asp Ile Pro Met Ser Asn Cys Phe Asn Ser
                    115                  120                125
        Gly Ile Asn Lys Ile Phe Val Met Ser Gln Phe Asn Ser Thr Ser Leu
                130                  135                140
        Asn Arg His Ile His Arg Thr Tyr Leu Glu Gly Ile Asn Phe Ala
        145                      150                  155                  160
        Asp Gly Ser Val Gln Val Leu Ala Ala Thr Gln Met Pro Glu Pro
                            165                  170                  175
        Ala Gly Trp Phe Gln Gly Thr Ala Asp Ser Ile Arg Lys Phe Ile Trp
                        180                  185                  190
        Val Leu Glu Asp Tyr Tyr Ser His Lys Ser Ile Asp Asn Ile Val Ile
                    195                  200                  205
        Leu Ser Gly Asp Gln Leu Tyr Arg Met Asn Tyr Met Glu Leu Val Gln
                210                  215                  220
        Lys His Val Glu Asp Asp Ala Asp Ile Thr Ile Ser Cys Ala Pro Val
        225                  230                  235                      240
        Asp Glu Ser Arg Ala Ser Lys Asn Gly Leu Val Lys Ile Asp His Thr
                            245                  250                  255
        Gly Arg Val Leu Gln Phe Phe Glu Lys Pro Lys Gly Ala Asp Leu Asn
                        260                  265                  270
        Ser Met Arg Val Glu Thr Asn Phe Leu Ser Tyr Ala Ile Asp Asp Ala
                    275                  280                  285
        Gln Lys Tyr Pro Tyr Leu Ala Ser Met Gly Ile Tyr Val Phe Lys Lys
                290                  295                  300
        Asp Ala Leu Leu Asp Leu Leu Lys Ser Lys Tyr Thr Gln Leu His Asp
        305                      310                  315                  320
        Phe Gly Ser Glu Ile Leu Pro Arg Ala Val Leu Asp His Ser Val Gln
                            325                  330                  335
        Ala Cys Ile Phe Thr Gly Tyr Trp Glu Asp Val Gly Thr Ile Lys Ser
                        340                  345                  350
        Phe Phe Asp Ala Asn Leu Ala Leu Thr Glu Gln Pro Ser Lys Phe Asp
                    355                  360                  365
        Phe Tyr Asp Pro Lys Thr Pro Phe Phe Thr Ala Pro Arg Cys Leu Pro
                370                  375                  380
        Pro Thr Gln Leu Asp Lys Cys Lys Met Lys Tyr Ala Phe Ile Ser Asp
        385                  390                  395                      400
        Gly Cys Leu Leu Arg Glu Cys Asn Ile Glu His Ser Val Ile Gly Val
                            405                  410                  415
        Cys Ser Arg Val Ser Ser Gly Cys Glu Leu Lys Asp Ser Val Met Met
                        420                  425                  430
        Gly Ala Asp Ile Tyr Glu Thr Glu Glu Ala Ser Lys Leu Leu Leu
                    435                  440                  445
        Ala Gly Lys Val Pro Ile Gly Ile Gly Arg Asn Thr Lys Ile Arg Asn
                450                  455                  460
        Cys Ile Ile Asp Met Asn Ala Arg Ile Gly Lys Asn Val Val Ile Thr
        465                      470                  475                  480
        Asn Ser Lys Gly Ile Gln Glu Ala Asp His Pro Glu Glu Gly Tyr Ser
                            485                  490                  495
        Tyr Tyr Ile Arg Ser Gly Ile Val Val Ile Leu Lys Asn Ala Thr Ile
                        500                  505                  510
        Asn Asp Gly Ser Val Ile
                    515
```

5,650,557

19                                                                          20

-continued ( 2 ) INFORMATION FOR SEQ ID NO:4:

( i ) SEQUENCE CHARACTERISTICS:
        ( A ) LENGTH: 1551 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
ATGCAGTTTG   CACTTGCATT   GGACACGAAC   TCAGGTCCTC   ACCAGATAAG   ATCTTGTGAG      60
GGTGATGGGA   TTGACAGGTT   GGAAAAATTA   AGTATTGGGG   GCAGAAAGCA   GGAGAAAGCT     120
TTGAGAAATA   GGTGCTTTGG   TGGTAGAGTT   GCTGCAACTA   CACAATGTAT   TCTTACCTCA     180
GATGCTTGTC   CTGAAACTCT   TCATTCTCAA   ACACAGTCCT   CTAGGAAAAA   TTATGCTGAT     240
GCAAACCGTG   TATCTGCGAT   CATTTGGGC    GGAGGCACTG   GATCTCAGCT   CTTTCCTCTG     300
ACAAGCACAA   GAGCTACGCC   TGCTGTACCT   GTTGGAGGAT   GTTACAGGCT   TATTGATATC     360
CCTATGAGTA   ACTGCTTCAA   CAGTGGTATA   AATAAGATAT   TGTGATGAG   TCAGTTCAAT      420
TCTACTTCGC   TTAACCGCCA   TATTCATCGT   ACATACCTTG   AAGGCGGGAT   CAACTTTGCT     480
GATGGATCTG   TACAGGTATT   AGCGGCTACA   CAAATGCCTG   AAGAGCCAGC   TGGATGGTTC     540
CAGGGTACAG   CAGACTCTAT   CAGAAAATTT   ATCTGGGTAC   TCGAGGATTA   TTACAGTCAC     600
AAATCCATTG   ACAACATTGT   AATCTTGAGT   GGCGATCAGC   TTTATCGGAT   GAATTACATG     660
GAACTTGTGC   AGAAACATGT   CGAGGACGAT   GCTGATATCA   CTATATCATG   TGCTCCTGTT     720
GATGAGAGCC   GAGCTTCTAA   AAATGGGCTA   GTGAAGATTG   ATCATACTGG   ACGTGTACTT     780
CAATTCTTTG   AAAAACCAAA   GGGTGCTGAT   TTGAATTCTA   TGAGAGTTGA   GACCAACTTC     840
CTGAGCTATG   CTATAGATGA   TGCACAGAAA   TATCCATACC   TTGCATCAAT   GGGCATTTAT     900
GTCTTCAAGA   AGATGCACT   TTTAGACCTT   CTCAAGTCAA   AATATACTCA   ATTACATGAC      960
TTTGGATCTG   AAATCCTCCC   AAGAGCTGTA   CTAGATCATA   GTGTGCAGGC   ATGCATTTTT    1020
ACGGGCTATT   GGGAGGATGT   TGGAACAATC   AAATCATTCT   TTGATGCAAA   CTTGGCCCTC    1080
ACTGAGCAGC   CTTCCAAGTT   TGATTTTTAC   GATCCAAAAA   CACCTTTCTT   CACTGCACCC    1140
CGATGCTTGC   CTCCGACGCA   ATTGGACAAG   TGCAAGATGA   AATATGCATT   TATCTCAGAT    1200
GGTTGCTTAC   TGAGAGAATG   CAACATCGAG   CATTCTGTGA   TTGGAGTCTG   CTCACGTGTC    1260
AGCTCTGGAT   GTGAACTCAA   GGACTCCGTG   ATGATGGGAG   CGGACATCTA   TGAAACTGAA    1320
GAAGAAGCTT   CAAAGCTACT   GTTAGCTGGG   AAGGTCCCGA   TTGGAATAGG   AAGGAACACA    1380
AAGATAAGGA   ACTGTATCAT   TGACATGAAT   GCTAGGATTG   GAAGAACGT   GGTGATCACA     1440
AACAGTAAGG   GCATCCAAGA   GGCTGATCAC   CCGGAAGAAG   GTCCTACTA   CATAAGGTCT     1500
GGAATCGTGG   TGATCCTGAA   GAATGCAACC   ATCAACGATG   GGTCTGTCAT   A              1551
```

( 2 ) INFORMATION FOR SEQ ID NO:5:

( i ) SEQUENCE CHARACTERISTICS:
        ( A ) LENGTH: 517 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
    Met   Gln   Phe   Ala   Leu   Ala   Leu   Asp   Thr   Asn   Ser   Gly   Pro   His   Gln   Ile
    1                 5                             10                            15
```

-continued

| | | | | | | | | | | | | | | |
|---|---|---|---|---|---|---|---|---|---|---|---|---|---|---|
|Arg|Ser|Cys|Glu 20|Gly|Asp|Gly|Ile|Asp 25|Arg|Leu|Glu|Lys|Leu 30|Ser|Ile|
|Gly|Gly|Arg 35|Lys|Gln|Glu|Lys|Ala 40|Leu|Arg|Asn|Arg|Cys 45|Phe|Gly|Gly|
|Arg|Val|Ala|Ala|Thr|Thr|Gln|Cys|Ile|Leu|Thr|Ser|Asp|Ala|Cys|Pro|
| |50| | | | |55| | | | | |60| | | |
|Glu|Thr|Leu|His|Ser|Gln|Thr|Gln|Ser|Ser|Arg|Lys|Asn|Tyr|Ala|Asp|
|65| | | | |70| | | | |75| | | | |80|
|Ala|Asn|Arg|Val|Ser|Ala|Ile|Ile|Leu|Gly|Gly|Gly|Thr|Gly|Ser|Gln|
| | | | |85| | | | |90| | | | |95| |
|Leu|Phe|Pro|Leu|Thr|Ser|Thr|Arg|Ala|Thr|Pro|Ala|Val|Pro|Val|Gly|
| | | |100| | | | |105| | | | |110| | |
|Gly|Cys|Tyr|Arg|Leu|Ile|Asp|Ile|Pro|Met|Ser|Asn|Cys|Phe|Asn|Ser|
| | | |115| | | | |120| | | | |125| | |
|Gly|Ile|Asn|Lys|Ile|Phe|Val|Met|Ser|Gln|Phe|Asn|Ser|Thr|Ser|Leu|
| | |130| | | | |135| | | | |140| | | |
|Asn|Arg|His|Ile|His|Arg|Thr|Tyr|Leu|Glu|Gly|Gly|Ile|Asn|Phe|Ala|
|145| | | | |150| | | | |155| | | | |160|
|Asp|Gly|Ser|Val|Gln|Val|Leu|Ala|Ala|Thr|Gln|Met|Pro|Glu|Glu|Pro|
| | | | |165| | | | |170| | | | |175| |
|Ala|Gly|Trp|Phe|Gln|Gly|Thr|Ala|Asp|Ser|Ile|Arg|Lys|Phe|Ile|Trp|
| | | |180| | | | |185| | | | |190| | |
|Val|Leu|Glu|Asp|Tyr|Tyr|Ser|His|Lys|Ser|Ile|Asp|Asn|Ile|Val|Ile|
| | |195| | | | |200| | | | |205| | | |
|Leu|Ser|Gly|Asp|Gln|Leu|Tyr|Arg|Met|Asn|Tyr|Met|Glu|Leu|Val|Gln|
| |210| | | | |215| | | | |220| | | | |
|Lys|His|Val|Glu|Asp|Asp|Ala|Asp|Ile|Thr|Ile|Ser|Cys|Ala|Pro|Val|
|225| | | |230| | | | |235| | | | | |240|
|Asp|Glu|Ser|Arg|Ala|Ser|Lys|Asn|Gly|Leu|Val|Lys|Ile|Asp|His|Thr|
| | | |245| | | | |250| | | | |255| | |
|Gly|Arg|Val|Leu|Gln|Phe|Phe|Glu|Lys|Pro|Lys|Gly|Ala|Asp|Leu|Asn|
| | |260| | | | |265| | | | |270| | | |
|Ser|Met|Arg|Val|Glu|Thr|Asn|Phe|Leu|Ser|Tyr|Ala|Ile|Asp|Asp|Ala|
| | |275| | | | |280| | | | |285| | | |
|Gln|Lys|Tyr|Pro|Tyr|Leu|Ala|Ser|Met|Gly|Ile|Tyr|Val|Phe|Lys|Lys|
| |290| | | | |295| | | | |300| | | | |
|Asp|Ala|Leu|Leu|Asp|Leu|Leu|Lys|Ser|Lys|Tyr|Thr|Gln|Leu|His|Asp|
|305| | | |310| | | | |315| | | | | |320|
|Phe|Gly|Ser|Glu|Ile|Leu|Pro|Arg|Ala|Val|Leu|Asp|His|Ser|Val|Gln|
| | | |325| | | | |330| | | | |335| | |
|Ala|Cys|Ile|Phe|Thr|Gly|Tyr|Trp|Glu|Asp|Val|Gly|Thr|Ile|Lys|Ser|
| | |340| | | | |345| | | | |350| | | |
|Phe|Phe|Asp|Ala|Asn|Leu|Ala|Leu|Thr|Glu|Gln|Pro|Ser|Lys|Phe|Asp|
| | |355| | | | |360| | | | |365| | | |
|Phe|Tyr|Asp|Pro|Lys|Thr|Pro|Phe|Phe|Thr|Ala|Pro|Arg|Cys|Leu|Pro|
| |370| | | | |375| | | | |380| | | | |
|Pro|Thr|Gln|Leu|Asp|Lys|Cys|Lys|Met|Lys|Tyr|Ala|Phe|Ile|Ser|Asp|
|385| | | | |390| | | | |395| | | | |400|
|Gly|Cys|Leu|Leu|Arg|Glu|Cys|Asn|Ile|Glu|His|Ser|Val|Ile|Gly|Val|
| | | |405| | | | |410| | | | |415| | |
|Cys|Ser|Arg|Val|Ser|Ser|Gly|Cys|Glu|Leu|Lys|Asp|Ser|Val|Met|Met|
| | |420| | | | |425| | | | |430| | | |
|Gly|Ala|Asp|Ile|Tyr|Glu|Thr|Glu|Glu|Glu|Ala|Ser|Lys|Leu|Leu|Leu|

|   | 435 |   |   |   |   | 440 |   |   |   |   | 445 |   |   |   |
|---|---|---|---|---|---|---|---|---|---|---|---|---|---|---|
| Ala | Gly 450 | Lys | Val | Pro | Ile | Gly 455 | Ile | Gly | Arg | Asn | Thr 460 | Lys | Ile | Arg | Asn |
| Cys 465 | Ile | Ile | Asp | Met | Asn 470 | Ala | Arg | Ile | Gly | Lys 475 | Asn | Val | Val | Ile | Thr 480 |
| Asn | Ser | Lys | Gly | Ile 485 | Gln | Glu | Ala | Asp | His 490 | Pro | Glu | Glu | Gly | Ser 495 | Tyr |
| Tyr | Ile | Arg | Ser 500 | Gly | Ile | Val | Val | Ile 505 | Leu | Lys | Asn | Ala | Thr 510 | Ile | Asn |
| Asp | Gly | Ser 515 | Val | Ile |   |   |   |   |   |   |   |   |   |   |   |

MATERIALS AND METHODS FOR INCREASING CORN SEED WEIGHT

CROSS-REFERENCE TO A RELATED APPLICATION

This application is a continuation-in-part of co-pending application Ser. No. 08/299,675, filed Sep. 1, 1994.

This invention was made with government support under National Science Foundation grant number 93052818. The government has certain rights in this invention.

BACKGROUND OF THE INVENTION

ADP-glucose pyrophosphorylase (AGP) catalyzes the conversion of ATP and α-glucose-1-phosphate to ADP-glucose and pyrophosphate. ADP-glucose is used as a glycosyl donor in starch biosynthesis by plants and in glycogen biosynthesis by bacteria. The importance of ADP-glucose pyrophosphorylase as a key enzyme in the regulation of starch biosynthesis was noted in the study of starch deficient mutants of maize (Zea mays) endosperm (Tsai and Nelson, 1966; Dickinson and Preiss, 1969).

AGP enzymes have been isolated from both bacteria and plants. Bacterial AGP consists of a homotetramer, while plant AGP from photosynthetic and non-photosynthetic tissues is a heterotetramer composed of two different subunits. The plant enzyme is encoded by two different genes, with one subunit being larger than the other. This feature has been noted in a number of plants. The AGP subunits in spinach leaf have molecular weights of 54 kDa and 51 kDa, as estimated by SDS-PAGE. Both subunits are immunoreactive with antibody raised against purified AGP from spinach leaves (Copeland and Preiss, 1981; Morell et al., 1987). Immunological analysis using antiserum prepared against the small and large subunits of spinach leaf showed that potato tuber AGP is also encoded by two genes (Okita et al., 1990). The cDNA clones of the two subunits of potato tuber (50 and 51 kDa) have also been isolated and sequenced (Muller-Rober et al., 1990; Nakata et al., 1991).

As Hannah and Nelson (Hannah and Nelson, 1975 and 1976) postulated, both Shrunken-2 (Sh2) (Bhave et al., 1990) and Brittle-2 (Bt2) (Bae et al., 1990) are structural genes of maize endosperm ADP-glucose pyrophosphorylase. Sh2 and Bt2 encode the large subunit and small subunit of the enzyme, respectively. From cDNA sequencing, Sh2 and Bt2 proteins have predicted molecular weight of 57,179 Da (Shaw and Hannah, 1992) and 52.224 Da, respectively. The endosperm is the site of most starch deposition during kernel development in maize. Sh2 and bt2 maize endosperm mutants have greatly reduced starch levels corresponding to deficient levels of AGP activity. Mutations of either gene have been shown to reduce AGP activity by about 95% (Tsai and Nelson, 1966; Dickinson and Preiss, 1969). Furthermore, it has been observed that enzymatic activities increase with the dosage of functional wild type Sh2 and Bt2 alleles, whereas mutant enzymes have altered kinetic properties. AGP is the rate limiting step in starch biosynthesis in plants. Stark et al. placed a mutant form of E. coli AGP in potato tuber and obtained a 35% increase in starch content (Stark, 1992).

The cloning and characterization of the genes encoding the AGP enzyme subunits have been reported for various plants. These include Sh2 cDNA (Bhave et al., 1990), Sh2 genomic DNA (Shaw and Hannah, 1992), and Bt2 cDNA (Bae et al., 1990) from maize; small subunit cDNA (Anderson et al., 1989) and genomic DNA (Anderson et al., 1991) from rice; and small and large subunit cDNAs from spinach leaf (Morell et al., 1987) and potato tuber (Muller-Rober et al., 1990; Nakata et al., 1991). In addition, cDNA clones have been isolated from wheat endosperm and leaf tissue (Olive et al., 1989) and Arabidopsis thaliana leaf (Lin et al., 1988).

AGP functions as an allosteric enzyme in all tissues and organisms investigated to date. The allosteric properties of AGP were first shown to be important in E. coli. A glycogen-overproducing E. coli mutant was isolated and the mutation mapped to the structural gene for AGP, designated as glyC. The mutant E. coli, known as glyC-16, was shown to be more sensitive to the activator, fructose 1,6 bisphosphate, and less sensitive to the inhibitor, cAMP (Preiss, 1984). Although plant AGP's are also allosteric, they respond to different effector molecules than bacterial AGP's. In plants, 3-phosphoglyceric acid (3-PGA) functions as an activator while phosphate ($PO_4$) serves as an inhibitor (Dickinson and Preiss, 1969).

In view of the fact that endosperm starch content comprises approximately 70% of the dry weight of the seed, alterations in starch biosynthesis correlate with seed weight. Unfortunately, the undesirable effect associated with such alterations has been an increase in the relative starch content of the seed. Therefore, the development of a method for increasing seed weight in plants without increasing the relative starch content of the seed is an object of the subject invention.

BRIEF SUMMARY OF THE INVENTION

The subject invention concerns a novel variant of the Shrunken-2 (Sh2) gene from maize. The Sh2 gene encodes ADP-glucose pyrophosphorylase (AGP), an important enzyme involved in starch synthesis in the major part of the corn seed, the endosperm. In a preferred embodiment, the novel gene of the subject invention encodes a variant AGP protein which has two additional amino acids inserted into the sequence. The variant gene described herein has been termed the Sh2-m1Rev6 gene. Surprisingly, the presence of the Sh2-m1Rev6 gene in a corn plant results in a substantial increase in corn seed weight when compared to wild type seed weight, but does so in the absence of an increase in the relative starch content of the kernel.

The subject invention further concerns a method of using the variant sh2 gene in maize to increase seed weight. The subject invention also concerns plants having the variant sh2 gene and expressing the mutant protein in the seed endosperm.

As described herein, the sh2 variant, Sh2-m1Rev6, can be produced using in vivo, site-specific mutagenesis. A transposable element was used to create a series of mutations in the sequence of the gene that encodes the enzyme. As a result, the Sh2-m1Rev6 gene encodes an additional amino acid pair within or close to the allosteric binding site of the protein.

BRIEF DESCRIPTION OF THE SEQUENCES

SEQ ID NO. 1 is the genomic nucleotide sequence of the Sh2-m1Rev6 gene.

SEQ ID NO. 2 is the nucleotide sequence of the Sh2-m1Rev6 cDNA.

SEQ ID NO. 3 is the amino acid sequence of the protein encoded by nucleotides 87 through 1640 of SEQ ID NO. 2.

SEQ ID NO. 4 is a nucleotide sequence encoding the amino acid sequence shown in SEQ ID NO. 5.

SEQ ID NO. 5 is the amino acid sequence of an ADP-glucose pyrophosphorylase (AGP) enzyme subunit containing a single serine insertion.

DETAILED DISCLOSURE OF THE INVENTION

The subject invention provides novel variants of the Shrunken-2 (Sh2) gene and a method for increasing seed weight in a plant through the expression of the variant sh2 gene. The Sh2 gene encodes a subunit of the enzyme ADP-glucose pyrophosphorylase (AGP) in maize endosperm. One variant gene, denoted herein as Sh2-m1Rev6, contains an insertion mutation that encodes an additional tyrosine:serine or serine:tyrosine amino acid pair that is not present in the wild type protein. The sequences of the wild type DNA and protein are disclosed in Shaw and Hannah, 1992. The in vivo, site-specific mutation which resulted in the tyrosine:serine or serine:tyrosine insertion, was generated in Sh2 using the transposable element, dissociation (Ds), which can insert into, and be excised from, the Sh2 gene under appropriate conditions. Ds excision can alter gene expression through the addition of nucleotides to a gene at the site of excision of the element.

In a preferred embodiment, insertion mutations in the Sh2 gene were obtained by screening for germinal revertants after excision of the Ds transposon from the gene. The revertants were generated by self-pollination of a stock containing the Ds-Sh2 mutant allele, the Activator (Ac) element of this transposable element system, and appropriate outside markers. The Ds element can transpose when the Ac element is present. Wild type seed were selected, planted, self-pollinated and crossed onto a tester stock. Results from this test cross were used to remove wild type alleles due to pollen contamination. Seeds homozygous for each revertant allele were obtained from the self-progeny. Forty-four germinal revertants of the Ds-induced sh2 mutant were collected.

Cloning and sequencing of the Ds insertion site showed that the nucleotide insertion resides in the area of the gene that encodes the binding site for the AGP activator, 3-PGA (Morrell, 1988). Of the 44 germinal revertants obtained, 28 were sequenced. The sequenced revertants defined 5 isoalleles of sh2: 13 restored the wild type sequence, 11 resulted in the insertion of the amino acid tyrosine, two contained an additional serine (inserted between amino acid residues 494 and 495, respectively, of the native protein sequence), one revertant contained a two amino acid insertion, tyrosine:tyrosine, and the last one, designated as Sh2-m1Rev6, contained the two amino acid insertion, tyrosine:serine or serine:tyrosine. The Sh2-m1Rev6 variant encodes an AGP enzyme subunit that has either the serine:tyrosine amino acid pair inserted between the glycine and tyrosine at amino acid residues 494 and 495, respectively, of the native protein, or the serine:tyrosine amino acid pair inserted between the two tyrosine residues located at position 495 and 496 of the native protein sequence. Due to the sequence of the amino acids in the area of the insertions, the Sh2-m1Rev6 variant amino acid sequences encoded by each of these insertions are identical to each other.

Surprisingly, the expression of the Sh2-m1Rev6 gene in maize resulted in a significant increase in seed weight over that obtained from maize expressing the wild-type Sh2 allele. Moreover, seeds from plants having the Sh2-m1Rev6 gene contained approximately the same percentage starch content relative to any of the other revertants generated. In a preferred embodiment, the Sh2-m1Rev6 gene is contained in homozygous form within the genome of a plant seed.

The subject invention further concerns a plant that has the Sh2-m1Rev6 gene incorporated into its genome. Other alleles disclosed herein can also be incorporated into a plant genome. In a preferred embodiment, the plant is a monocotyledonous species. More preferably, the plant may be *Zea mays*. Plants having the Sh2-m1Rev6 gene can be grown from seeds that have the gene in their genome. In addition, techniques for transforming plants with a gene are known in the art.

Because of the degeneracy of the genetic code, a variety of different polynucleotide sequences can encode the variant AGP polypeptide disclosed herein. In addition, it is well within the skill of a person trained in the art to create alternative polynucleotide sequences encoding the same, or essentially the same, polypeptide of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by Sh2-m1Rev6 or the other alleles. The subject invention also contemplates those polynucleotide molecules having sequences which are sufficiently homologous with the wild type Sh2 DNA sequence so as to permit hybridization with that sequence under standard high-stringency conditions. Such hybridization conditions are conventional in the art (see, e.g., Maniatis et al., 1989).

The polynucleotide molecules of the subject invention can be used to transform plants to express the Sh2-m1Rev6 allele, or other alleles of the subject invention, in those plants. In addition, the polynucleotides of the subject invention can be used to express the recombinant variant AGP enzyme. They can also be used as a probe to detect related enzymes. The polynucleotides can also be used as DNA sizing standards.

The polypeptides encoded by the polynucleotides of the subject invention can be used to catalyze the conversion of ATP and α-glucose-1-phosphate to ADP-glucose and pyrophosphate, or to raise an immunogenic response to the AGP enzymes and variants thereof. They can also be used as molecular weight standards, or as an inert protein in an assay.

The following are examples which illustrate procedures and processes, including the best mode, for practicing the invention. These examples should not be construed as limiting, and are not intended to be a delineation of all possible modifications to the technique. All percentages are by weight and all solvent mixture proportions are by volume unless otherwise noted.

Example 1—Expression of Sh2-m1Rev6 Gene in Maize Endosperm.

Homozygous plants of each revertant obtained after excision of the Ds transposon were crossed onto the F1 hybrid corn, "Florida Stay Sweet." This sweet corn contains a null allele for the Sh2 gene, termed sh2-R. Resulting endosperms contained one dose of the functional allele from a revertant and two female-derived null alleles, denoted by the following genotype Sh2-m1RevX/sh2-R/sh2-R, where X represents one of the various isoalleles of the revertants. Crosses were made during two growing seasons.

Resulting seed weight data for each revertant and wild type seed are shown in Table 1. The first column shows the amino acid insertion in the AGP enzyme obtained after the in vivo, site-specific mutagenesis.

TABLE 1

| Sequence alteration | # of revertants | Average Seed weight | Standard deviation |
|---|---|---|---|
| wild type | 13 | 0.250 grams | 0.015 |
| tyrosine | 11 | 0.238 grams | 0.025 |
| serine | 2 | 0.261 grams | 0.014 |
| tyr, tyr | 1 | 0.223 grams | nd* |
| tyr, ser (Rev6) | 1 | 0.289 grams | 0.022 |

*nd = not determined

The data shown in Table 1 represents the average kernel seed weight for each revertant over the course of two growing seasons. The expression of the Sh2-m1Rev6 gene to produce the Rev6 mutant AGP subunit gave rise to an almost 16% increase in seed weight in comparison to the wild type revertant. The revertants having the single serine insertion also showed an increase in average seed weight over wild type seed weight.

In addition, starch content was determined on the kernels analyzed above using various methodologies. The analysis showed that Sh2-m1Rev6 containing kernels were no higher in percentage starch relative to kernels expressing the other alleles shown in the table above. Therefore, it appears that the increase in seed weight is not solely a function of starch content.

Corn seeds that contain at least one functional Sh2-m1Rev6 allele encoding the tyrosine:serine insertion mutation in the AGP enzyme subunit have been deposited with the American Type Culture Collection (ATCC), 12301 Parklawn Drive, Rockville, Md. 20852 USA.

The seeds have been deposited under conditions that assure that access to the seeds will be available during the pendency of this patent application to one determined by the Commissioner of Patents and Trademarks to be entitled thereto under 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject seed deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the seed. The depositor acknowledges the duty to replace the deposit should the depository be unable to furnish a sample when requested, due to the condition of the deposit. All restrictions on the availability to the public of the subject seed deposit will be irrevocably removed upon the granting of a patent disclosing it.

As would be apparent to a person of ordinary skill in the art, seeds and plants that are homozygous for the Sh2-m1Rev6 allele can be readily prepared from heterozygous seeds using techniques that are standard in the art. In addition, the Sh2-m1Rev6 gene can be readily obtained from the deposited seeds.

The skilled artisan, using standard techniques known in the art, can also prepare polynucleotide molecules that encode additional amino acid residues, such as serine, at the location of the insertions in the subject revertants. Such polynucleotide molecules are included within the scope of the subject invention.

It should be understood that the examples and embodiments described herein are for illustrative purposes only and that various modifications or changes in light thereof will be suggested to persons skilled in the art and are to be included within the scope and purview of this application and the scope of the appended claims.

References

Anderson, J. M., J. Hnilo, R. Larson, t. W. Okita, M. Morell, J. Preiss (1989) "The encoded primary sequence of a rice seed ADP-glucose pyrophosphorylase subunit and its homology to the bacterial enzyme." *J. Biol. Chem.* 264:12238–12242.

Anderson, J. M., R. Larson, D. Landencia, W. T. Kim, D. Morrow, T. W. Okita, J. Preiss (1991) "Molecular characterization of the gene encoding a rice endosperm-specific ADP-glucose pyrophosphorylase subunit and its developmental pattern of transcription." *Gene* 97:199–205.

Bae, J. M., M. Giroux, L. C. Hannah (1990) "Cloning and characterization of the Brittle-2 gene of maize." *Maydica* 35:317–322.

Bhave, M. R., S. Lawrence, C. Barton, L. C. Hannah (1990) "Identification and molecular characterization of Shrunken-2 cDNA clones of maize." *Plant Cell* 2:581–588.

Copeland, L., J. Preiss (1981) "Purification of spinach leaf ADP-glucose pyrophosphorylase." *Plant Physiol.* 68:996–1001.

Dickinson, D. B., J. Preiss (1969) "Presence of ADP-glucose pyrophosphorylase in Shrunken-2 and Brittle-2 mutants of maize endosperm." *Plant Physiol.* 44:1058–1062.

Hannah, L. C., O. E. Nelson (1975) "Characterization of adenosine diphosphate glucose pyrophosphorylase from developing maize seeds." *Plant Physiol.* 55:297–302.

Hannah, L. C., O. E. Nelson (1976) "Characterization of adenosine diphosphate glucose pyrophosphorylase from Shrunken-2 and Brittle-2 mutants of maize." *Biochem. Genet.* 14:547–560.

Lin, T., T. Caspar, C. Somerville, J. Preiss (1988) "A starch deficient mutant of *Arabidopsis thaliana* with low ADP-glucose pyrophosphorylase activity lacks one of the two subunits of the enzyme." *Plant Physiol.* 88:1175–1181.

Maniatis, T., E. F. Fritsch, J. Sambrook (1989) *Molecular Cloning: A Laboratory Manual*, 2d Edition, Cold Spring Harbor Laboratory, Cold Spring Harbor, N.Y.

Morell, M., M. Bloon, V. Knowles, J. Preiss (1988) "Subunit structure of spinach leaf ADP-glucose pyrophosphorylase." *J. Bio. Chem.* 263:633.

Muller-Rober, B. T., J. Kossmann, L. C. Hannah, L. Willmitzer, U. Sounewald (1990) "One of the two different ADP-glucose pyrophosphorylase genes from potato responds strongly to elevated levels of sucrose." *Mol. Gen. Genet.* 224:136–146.

Nakata, P. A., T. W. Greene, J. M. Anderson, B. J. Smith-White, T. W. Okita, J. Preiss (1991) "Comparison of primary sequences of two potato tuber ADP-glucose pyrophosphorylase subunits." *Plant Mol. Biol.* 17:1089–1093.

Okita, T. W., P. A. Nakata, J. M. Anderson, J. Sowokinos, M. Morell, J. Preiss (1990) "The subunit structure of potato tuber ADP-glucose pyrophosphorylase." *Plant Physiol.* 93:785–790.

Olive, M. R., R. J. Ellis, W. W. Schuch (1989) "Isolation and nucleotide sequences of cDNA clones encoding ADP-glucose pyrophosphorylase polypeptides from wheat leaf and endoosperm." *Plant Physiol. Mol. Biol.* 12:525–538.

Preiss, J. (1984) "Bacterial glycogen synthesis and it regulation," *Ann. Rev. Microbiol.* 419–458.

Shaw, J. R., L. C. Hannah (1992) "Genomic nucleotide sequence of a wild type Shrunken-2 allele of *Zea mays*," *Plant Physiol.* 98:1214–1216.

Starke, et al. (1992) "Regulation of the amount of starch in plant tissues by ADP-glucose pyrophosphorylase," *Science* 258:287.

Tsai, C., O. E. Nelson (1966) "Starch-deficient maize mutant lacking adenosine diphosphate glucose pyrophosphorylase activity," *Science* 151:341–343.

We claim:

1. A polynucleotide molecule, comprising a variant of the wild type shrunken-2 (Sh2) gene, wherein said variant codes for the insertion of at least one additional amino acid within the allosteric binding site of the ADP-glucose pyrophosphorylase (AGP) enzyme subunit, whereby a plant expressing said polynucleotide molecule has increased seed weight relative to the seed weight of a plant expressing the wild type Sh2 gene.

2. The polynucleotide molecule, according to claim 1, wherein said polynucleotide molecule encodes at least one serine residue inserted between amino acids 494 and 495 of the native AGP enzyme subunit.

3. The polynucleotide molecule, according to claim 1, wherein said polynucleotide molecule encodes the amino acid pair tyrosine:serine, wherein said amino acid pair is inserted between amino acids 494 and 495 of the native AGP enzyme subunit.

4. The polynucleotide molecule, according to claim 1, wherein said polynucleotide molecule encodes the amino acid pair serine:tyrosine, wherein said amino acid pair is inserted between amino acids 495 and 496 of the native AGP enzyme subunit.

5. The polynucleotide molecule, according to claim 1, wherein the AGP enzyme encoded by said polynucleotide molecule consists essentially of an amino acid sequence selected from the group consisting of SEQ ID NO. 5 and SEQ ID NO. 3.

6. The polynucleotide molecule, according to claim 5, wherein the nucleotide sequence encoding SEQ ID NO. 3 comprises nucleotides 87 through 1640 of the sequence shown in SEQ ID NO. 2, or a degenerate fragment thereof, wherein seeds produced by a plant expressing said polynucleotide molecule exhibit increased seed weight relative to the seed weight of seeds produced by a plant expressing the wild type Sh2 gene.

7. A method for increasing the seed weight of a plant, comprising incorporating the polynucleotide molecule of claim 1 into the genome of said plant and expressing the protein encoded by said polynucleotide molecule.

8. The method, according to claim 7, wherein said plant is *Zea mays*.

9. A plant seed comprising the polynucleotide molecule of claim 1 within the genome of said seed.

10. A plant expressing the polynucleotide molecule of claim 1.

11. The plant, according to claim 10, wherein said plant is *Zea mays*.

12. The plant, according to claim 10, wherein said plant is grown from the seed of claim 9.

* * * * *

UNITED STATES PATENT AND TRADEMARK OFFICE
CERTIFICATE OF CORRECTION

PATENT NO. : 5,650,557

DATED : July 22, 1997

INVENTOR(S) : L. Curtis Hannah and Michael Giroux

It is certified that error appears in the above-identified patent and that said Letters Patent is hereby corrected as shown below:

Column 2, line 53: "within or dose" should read --within or close--.

Column 5, line 33: "USA." should read --USA, on May 16, 1996 and assigned ATCC accession number ATCC 97624. Seeds having at least one allele encoding the serine insertion mutation in the AGP enzyme subunit have also been deposited with ATCC on May 16, 1996 and assigned ATCC accession number ATCC 97625.--

Signed and Sealed this

Eleventh Day of November, 1997

*Attest:*

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,650,557 Page 1 of 1
DATED : July 22, 1997
INVENTOR(S) : L. Curtis Hannah and Michael Giroux It is certified that error appears in the above-identified patent and that said Letters Patent is hereby corrected as shown below:

Column 3,
Lines 47-48, "serine:tyrosine" should read -- tyrosine:serine --.

Signed and Sealed this

Twenty-ninth Day of April, 2003

JAMES E. ROGAN
*Director of the United States Patent and Trademark Office*